(12) United States Patent
Paulsen et al.

(10) Patent No.: US 8,293,265 B2
(45) Date of Patent: *Oct. 23, 2012

(54) PROCESS FOR MANUFACTURING CHEWABLE DOSAGE FORMS FOR DRUG DELIVERY AND PRODUCTS THEREOF

(75) Inventors: Neil E. Paulsen, Johns Island, SC (US); Roland Johnson, Lexington, NC (US); Michael Coffee, Greensboro, NC (US)

(73) Assignee: Bayer B.V., Mijdrecht (NL)

(*) Notice: Subject to any disclaimer, the term of this patent is extended or adjusted under 35 U.S.C. 154(b) by 266 days.

This patent is subject to a terminal disclaimer.

(21) Appl. No.: 12/506,165

(22) Filed: Jul. 20, 2009

(65) Prior Publication Data

US 2009/0280159 A1 Nov. 12, 2009

Related U.S. Application Data

(63) Continuation of application No. 11/296,181, filed on Dec. 7, 2005, now abandoned.

(51) Int. Cl.
*A61K 47/00* (2006.01)
*A61K 47/44* (2006.01)

(52) U.S. Cl. ..................................... 424/439
(58) Field of Classification Search .................. None
See application file for complete search history.

(56) References Cited

U.S. PATENT DOCUMENTS

| | | |
|---|---|---|
| 3,486,186 A | 12/1969 | Richards et al. |
| 3,887,964 A | 6/1975 | Richards |
| 3,952,478 A | 4/1976 | Richards et al. |
| 4,054,967 A | 10/1977 | Sandberg et al. |
| 4,097,961 A | 7/1978 | Richards |
| 4,182,003 A | 1/1980 | Lamartino et al. |
| 4,306,883 A | 12/1981 | Eckman |
| 4,334,339 A | 6/1982 | Holly |
| 4,338,702 A | 7/1982 | Holly |
| 4,343,068 A | 8/1982 | Holly |
| 4,356,595 A | 11/1982 | Sandberg et al. |
| 4,372,008 A | 2/1983 | Sandberg |
| 4,535,505 A | 8/1985 | Holly et al. |
| 4,597,135 A | 7/1986 | Holly et al. |
| 4,608,731 A | 9/1986 | Holly |
| 4,622,717 A | 11/1986 | Bollinger |
| 4,697,308 A | 10/1987 | Sandberg |
| 4,710,390 A | 12/1987 | Schumacher et al. |
| 4,724,150 A | 2/1988 | Knebl et al. |
| 4,768,941 A | 9/1988 | Wagner |
| 4,780,931 A | 11/1988 | Powers et al. |
| 4,800,087 A | 1/1989 | Mehta |
| 4,818,446 A | 4/1989 | Schreiber et al. |
| 4,821,376 A | 4/1989 | Sandberg |
| 4,872,241 A | 10/1989 | Lindee |
| 4,975,039 A | 12/1990 | Dare et al. |
| 4,996,743 A | 3/1991 | Janssen |
| 5,021,025 A | 6/1991 | Wagner |
| 5,022,888 A | 6/1991 | Lindee |
| 5,320,848 A | 6/1994 | Geyer et al. |
| 5,380,535 A | 1/1995 | Geyer et al. |
| 5,637,313 A | 6/1997 | Chau et al. |
| 5,655,436 A | 8/1997 | Soper |
| 5,735,603 A | 4/1998 | Kesig et al. |
| 5,747,061 A | 5/1998 | Amselem et al. |
| 5,753,255 A * | 5/1998 | Chavkin et al. ............... 424/441 |
| 5,980,228 A | 11/1999 | Soper |
| 6,340,471 B1 | 1/2002 | Kershman et al. |
| 6,344,222 B1 | 2/2002 | Cherukuri et al. |
| 6,352,713 B1 * | 3/2002 | Kirschner et al. ............. 424/441 |
| 6,495,177 B1 * | 12/2002 | deVries et al. .................. 426/72 |
| 6,613,346 B2 | 9/2003 | Seielstad et al. |
| 6,672,252 B2 | 1/2004 | Levin et al. |
| 6,777,401 B2 | 8/2004 | Hanna |
| 6,868,136 B2 | 3/2005 | Hansen et al. |
| 7,258,879 B1 * | 8/2007 | Hodge et al. ....................... 426/2 |
| 7,955,632 B2 * | 6/2011 | Paulsen et al. ................. 426/514 |
| 8,114,445 B2 * | 2/2012 | Hastings ........................ 424/725 |

FOREIGN PATENT DOCUMENTS

EP 1 675 474 B1 10/2008
WO WO 2005/094210 10/2005

OTHER PUBLICATIONS

Article entitled "Fluidized Bed Mixing Techniques," published online Feb. 2, 2001, website address: http://www.chemicalonline.com/article.mvc/Fluidized-Bed-Mixing-Technique-00001.
Balabudkin et al., "Improvement in the Technology of Manufacturing Ointments Containing Antibiotics," (1979), Plenum Publishing Corporation.
Chung et al., "Frictional Behavior of Solid Polymers on a Metal Surface at Processing Conditions," *Polymer Engineering and Science* (1977), 17:9-20.
Derezinski, S., "The Compressibility of the Resin Solid Feed Bed in Extrusion," *Conference Proceedings, ANTEC '88, Society of Plastics Engineers* (1988), 105-108.
Derezinski et al., "Heat Transfer Coefficients in Extruder Melt Sections," *Conference Proceedings, ANTEC '96, Society of Plastics Engineers* (1996), 417-421.
Derezinski, Stephen J., "Calculating Power of Extruder Melt Sections," *Journal of Materials Processing & Manufacturing Science* (1997), 6:71-77.
Forberg Fluidized Zone Mixers Manual, American Process Systems (Apr. 1999).
Handbook of Pharmaceutical Excipients; *American Pharmaceutical Association*, Ascorbic Acid (1986), 6-8.
Handbook of Pharmaceutical Excipients; *American Pharmaceutical Association*, Glycerin (1986), 123.
Lindt, J.T., "Mathematical Modeling of Melting Polymers in Single-Screw Extruders: A Critical Review," *Conference Proceedings, ANTEC '84, Society of Plastics Engineers* (1984), 73-76.

(Continued)

*Primary Examiner* — Anand Desai
*Assistant Examiner* — Melissa Mercier
(74) *Attorney, Agent, or Firm* — DLA Piper LLP (US)

(57) ABSTRACT

A palatable, soft chewable medication vehicle for delivery of a pharmaceutically acceptable active ingredient, such as a drug, to an animal or human subject. The soft chews contain only food grade or better inactive ingredients, and preferably do not contain ingredients of animal origin. Processes for manufacturing the soft chews do not require the generation of heat during mixing of active and inactive ingredients, provide stable concentrations of the active ingredient, and produce chews of consistent weight and texture.

26 Claims, No Drawings

OTHER PUBLICATIONS

Miller and White, "Heat Transfer in the Transition Section of a Plasticating Extruder," *Conference Proceedings, ANTEC '74, Society of Plastics Engineers* (1974), 243-246.

Mount III et al., "Analytical Melting Model for Extrusion: Melting Rate of Fully Compacted Solid Polymers," *Polymer Engineering and Science* (1982), 22(12):729-737.

Paulsen, Neil, Declaration, Apr. 1, 2009.

Rauwendaal, C., "Dispersed Solids Melting Theory," *Conference Proceedings, ANTEC '93, Society of Plastics Engineers* (1993), 2232-2237.

Vermeulen et al., "The Melting of a Crystalline Polymer in a Screw Extruder," *Chemical Engineering Science* (1971), 26:1457-1465, Pergamon Press.

* cited by examiner

PROCESS FOR MANUFACTURING CHEWABLE DOSAGE FORMS FOR DRUG DELIVERY AND PRODUCTS THEREOF

RELATED APPLICATION

Under 35 USC §120, this application is a continuation application of U.S. application Ser. No. 11/296,181, filed Dec. 7, 2005, now pending, which is hereby incorporated by reference it its entirety.

FIELD OF THE INVENTION

The invention relates to the field of orally administrable pharmaceutical dosage units; in particular, units in the form of an edible mass, such as a chunk.

BACKGROUND OF THE INVENTION

Formulation of a drug into an edible medication, such as a chewable tablet or confection, can increase patient acceptance of the medication, especially animals, who tend to resist swallowing hard tablets or capsules. Unfortunately, many drugs and other active ingredients (collectively, "actives") have a strongly bitter or otherwise unpalatable taste, making chewing them unpleasant.

Flavorings are commonly added to chewable medications to enhance their palatability. For example, a veterinary medication might include animal product-based flavorings such as uncooked dried meat parts such as beef, pork, chicken, turkey, fish and lamb; organ meats such as liver; meat meals, bone meals and ground bone; and animal-derived food such as casein, milk (which may include dry forms and lowered fat forms, such as dry skim milk), yogurt, gelatin, cheese and egg (collectively, "animal origin flavorings") may be utilized.

However, use of many animal origin flavorings (especially of meat, poultry or seafood origin) risks exposure to infectious agents, not only to the recipient of the drug, but also through contamination of manufacturing equipment on which the flavored dosage units are made. For this reason, manufacturing facilities that prepare pharmaceutical products with animal origin flavorings are often devoted exclusively to their preparation, at a correspondingly greater cost than would be incurred if manufacturing could be performed in a facility capable of concurrently processing multiple products.

Texture is also an issue for chewable medications. One of the most commonly used form for chewable dosage units is the compressed tablet, whose ingredients (including the actives and inactive ingredients such as binders) can make the tablet gritty or otherwise unappealing, especially to animals. Thus, a preferred alternative dosage form for use especially with animals is the "soft chew," generally a meat-like mass or chunk also widely found in consumable pet treats.

Soft chews are typically manufactured by blending and extrusion. Pre-mixed ingredients are introduced into an extruder barrel with a screw therein, then mixed, coagulated, expanded and sheared into a blended mixture, followed by application of additional heat if a harder texture is desired. Water introduced into the mixture must generally be of pharmaceutical grade, as it will be retained within the mixture. The blended mixture is then formed into a desired shape on a die plate, then cut into individual units.

The heat generated during the extrusion process can cause deterioration in the stability (potency or integrity) of the active in the mixture, causing the effective dose provided by each unit formed to vary. Consistency of texture, shape and weights of the chews from batch to batch of extruded material can also suffer.

There is a need, therefore, for a method of manufacture for soft chewable medications in which the blending of actives into the chew mixture is achieved without generation of heat. It is also desirable that the chews be susceptible to manufacture without use of costly, pharmaceutical grade water as an ingredient. There is also a need in the art for a soft chew medication whose taste appeals to animals without use of ingredients that may include infectious agents or contaminants. Further, it is highly desirable for the manufacturing means employed to produce chewable medications to do so in a manner that ensures consistent chew weights, texture and active dosages.

SUMMARY OF THE INVENTION

The invention provides a unique soft chew medication and processes for its manufacture. The soft chews of the invention are particularly palatable to pet animals. They contain inactive ingredients of at least food grade quality, and most preferably do not contain inactive ingredients of animal origin. As such, the soft chews may be manufactured without concern about transmission of infectious agents or contaminants, and without risk of cross-contaminating other products produced in the same manufacturing facility.

The manufacturing processes of the invention allow the soft chews to be produced without application of heat to the ingredient mixture. Stability of the actives is therefore preserved, and a well-blended, soft texture is provided. Further, no water is used as an ingredient of the chews, thereby avoiding the need for use of costly pharmaceutical grade water, while reducing the opportunity for microbial growth or loss of potency by the active.

To these ends, the soft chews of the invention are manufactured using large capacity horizontal mixers which spins the chew mixture into particulate form. The mixing action causes the ingredients in the mixture to be cast away from the mixing vessel walls, crisscrossing the vessel to provide a uniformly blended mixture formed without application of heat. Because no cooling step is required, the time to produce chews is shortened compared to cooking extrusion methods.

The highly blended mixture produced is placed into molds to form individual dosage units and allowed to set without application of heat. Soft chews can be produced in any desired shape. Preferred mixing and molding equipment utilized in the invention can provide individual soft chews with consistently blended ingredients, stably provided actives and consistent weights.

The soft chews of the invention are produced in palatable form without the use of any non-food grade inactive ingredients (or, preferably, any animal origin inactive ingredients). The manufacturing processes may therefore be performed without risk of potential cross-contamination of other equipment in the facility with infectious agents or contaminants derived from sources such as the animal-origin meat flavorings commonly used in chewable medications for animals.

DETAILED DESCRIPTION OF THE INVENTION

A. Materials for Use in Soft Chews of the Invention

In general, soft chewable medications and treats include as inactive ingredients matter such as binding agents, vitamins, and colors to enhance the manufacturability, texture and appearance of the product. Those of ordinary skill in the art will be familiar with such inactive ingredients, which need not include water for use in the invention.

For use in the invention, no inactive ingredients of the soft chew should be of less than food grade quality and may be of higher quality (e.g., USP or NF grade). In this context, "food grade" refers to material that does not contain or impart chemicals or agents hazardous to health. Thus, a food grade flavoring, if of animal origin, will be one that has been prepared to substantially reduce or eliminate the presence of infectious agents or contaminants therein; e.g., by processes such as pasteurization, pressurization or irradiation.

The latter process in particular can effectively eliminate infectious agents such as *E. coli* O157:H7, *Salmonella* and *Campylobacter* from a wide variety of food and animal-derived substances, such as raw meat products, vegetables, grains and fruits. Preferably, however, soft chews of the invention will not contain any animal origin ingredients, and most preferably will not contain any animal origin flavorings. All ingredients should be pharmaceutically acceptable (e.g., food grade, USP or NF, as appropriate).

Flavorings are preferably present in soft chews of the invention that are at least food grade in quality, and most preferably exclude animal origin flavorings. Preferred non-animal origin flavorings are plant proteins, such as soy protein, to which edible artificial food-like flavorings has been added (e.g., soy-derived bacon flavoring). Depending on the target animal, other non-animal flavorings could include anise oil, carob, peanuts, fruit flavors, sweeteners such as honey, sugar, maple syrup and fructose, herbs such as parsley, celery leaves, peppermint, spearmint, garlic, or combinations thereof.

A particularly preferred flavoring for use in the invention is Provesta™ 356, made by ABF Ingredients, Inc. It is a light tan, water-soluble powder that builds on the properties of yeast extracts and reaction flavors to provide a pleasant smoky, cured bacon flavor. Provesta 356 contains no animal derived ingredients.

For administration to horses and other grazing animals, as well as small animals such as rabbits, hamsters, gerbils, and guinea pigs, grains and seeds are especially appealing additional flavoring agents. The grains may be present in any form consistent with the production of the chew including flour, bran, cereal, fiber, whole grain and meal forms, including gluten meals, and may be rolled, crimped, ground, dehydrated or milled. Minerals may also be added as flavorings, such as salt and other spices. Preferably, the grain utilized is dehydrated, milled or flaked. Vegetables such as dehydrated carrots and seeds such as safflower seeds or milo seeds are especially appealing to small animals and may be included.

Further, agents which enhance the manufacturability and texture of a soft chew may include softening agents, an anti-caking agent or lubricant, and a humectant or wetting agent. Illustrative examples of lubricants or anti-caking agents which may be used in the invention include magnesium stearate, calcium stearate, solid polyethylene glycols, sodium lauryl sulfate, or mixtures thereof. Magnesium stearate is particularly preferred for lubrication and as a component to aid in setting the soft chews after molding.

Humectants illustratively include glycerol and propylene glycol, and wetting agents include cetyl alcohol and glycerol monostearate. Glycerin is a preferred humectant useful in maintaining the softness of the soft chew over the shelf life of the product. Glycerin is a clear, colorless, odorless, viscous, hygroscopic liquid.

Vegetable oils (such as corn, safflower, cottonseed, soybean and olive oils) may also be utilized to lubricate the chew mixture and maintain its softness. Oil also aids in flavor palatability. A particularly preferred oil is soybean oil.

Paraffin wax or polyethylene glycol 8000 (carbowax) will preferably be included in the soft chew mixture before molding at 1.0% to 3.0%. If wax is used, it is melted at 50° C. before being added to the soft chew mixture after mixing. After molding, the soft chews with the added wax will set-up, usually over a period of 8 to 24 hours. The wax congeals quickly, softens the chew mixture, and prevents the soft chew units from sticking together after molding.

Additional softening agents utilized are those which limit density and hardness of the soft chew product. Such agents may include polysaccharides and fiber. A polysaccharide may be included in the form of a complex food such as a fruit, a plant starch such as potato or tapioca starch. Polysaccharide may also be provided separately, for example, in the form of chondroitin sulfate or glucosamine HCl.

Fiber may be also provided as filler or as a bulking agent and to provide or maintain porosity in the soft chew. Fibers used to this end may be derived from fruits, grains, legumes, vegetables or seeds, or provided in forms such as wood fiber, paper fiber or cellulose fiber such as powdered cellulose fiber. A particularly preferred such bulking agent for use in the invention is bran, such as oat bran.

Other bulking agents that may be utilized include any food grade material, including hydrocolloid thickeners and binders, such as gum arabic, pectins, modified starches, alginates, carrageenans, xanthan gums, carboxymethylcellulose, methylcellulose, hydroxyethylcellulose, hydroxypropylcellulose, hydroxypropylmethylcellulose, propylene glycol alginate, polyvinylpyrrolidone (PVP), carboxyvinyl polymers (such as Carbopol®), polyethylene oxide polymers (such as Polyox®), talc, dicalcium phosphate, and antacids.

Binders utilized in soft chews may be a sticky substance or a substance which becomes sticky in combination with other ingredients such as water, but will preferably give the soft chew product a food-like texture. In general, binders may include molasses, corn syrup, peanut butter, food gum, a starch such as potato starch, tapioca starch or corn starch, honey, maple syrup and sugars. Preferred binders for use in soft chews of the invention are starches and powdered sweeteners.

A particularly preferred binder is Starch 1500, a pregelatinized starch made by Colorcon Corporation. Pregelatinized starch is a starch that has been chemically and/or mechanically modified to rupture all or part of the starch granules and so render the starch flowable. It contains 5% of free amylase, 15% of free amylopectin and 80% unmodified starch. The source is from corn.

Powdered sugar (sucrose) serves well as a sweetener as well as a binder. Sucrose is obtained from either sugar cane or sugar beets. Salt and/or other spices may be added as appropriate, with salt being especially preferred to enhance flavor.

A preservative such as potassium sorbate, sodium benzoate or calcium propionate may be included in order to retard growth of microorganisms and fingi Tenox 4 is a combination of BHA and BHT anti-oxidants, made by Eastman Chemicals. It is a preferred and convenient preservation system.

Vitamins may be provided according to the nutritional requirements of the target animal, and may be provided as an element of oils utilized. Vitamins are also present in various oils that may be added as softening agents; for example, canola oil, corn oil, soybean oil and vegetable oil.

Excipients that may be utilized include starches, cellulose, or derivatives or mixtures thereof, in amounts ranging, for example, from about 1 to about 60 percent (w/w), preferably from about 2 to about 50 percent, more preferably from about 15 to 50 percent. For example, the excipient may consist of sodium starch glycolate, pregelatinized corn starch (Starch 1500), crospovidone (Polyplasdone XL™, International Specialty Products), and croscarmellose sodium (Ac-Di-Sol™, FMC Corp.), and derivatives thereof. Excipients may be used to create a trituration of an active. For example, to create a 10% trituration, 100 grams of the active is combined with 900 grams of an excipient, such as a preferred excipient, Starch 1500. The dry mixture is fluidized and is then preferably coated.

If a coating is to be provided (to help protect the stability of the active and mask its taste), food grade coatings are preferred, such as an aqueous film coat from Colorcon Corporation sold as OPADRY™. OPADRY is a methylcellulose based product with a plasticizer and pigment. Since the coating is aqueous based, no special handling precautions are required during manufacture of the soft chew. However, after administration, the aqueous film coat will start to erode and/or dissolve within minutes when exposed to water or other liquids in the stomach. Therefore, disintegration and dissolution of the soft chew should not be delayed after it is administered to the subject.

Any orally administrable active drug or other biologically active compound may be provided in the soft chews of the invention. Those of ordinary skill in the human and/or veterinary pharmaceutical arts will be entirely familiar with the identity of such actives which may include, without limitation, antibiotics, analgesics, antivirals, antifungals, anthelmetics, endo- and ecto-parasticides, hormones and/or derivatives thereof, anti-inflammatories (including non-steroidal anti-inflammatories), steroids, behavior modifiers, vaccines, antacids, laxatives, anticonvulsants, sedatives, tranquilizers, antitussives, antihistamines, decongestants, expectorants, appetite stimulants and suppressants, minerals and vitamins.

The amounts of each of the components in the final product may be varied considerably, depending upon the nature of the drug, the weight and condition of the subject treated, and the unit dosage desired. Those of ordinary skill in the art will be able to adjust dosage amounts for particular actives in the soft chews in light of the teachings of this disclosure. Generally, however, the active may be provided by range in weight based on the total weight of the composition from about 0.001% to 75% (w/w), more preferably 0.095% to 40%, and most preferably not in excess of 50%. For example, for administration of an anthelmetic to dogs, such as ivermectin for treatment of heartworms (see, Example 1) triturated with starch could be added to comprise 31.2% of the foregoing mixture.

The formula described for the exemplary product may be easily modified for delivery of actives to other species. For example, equine soft chews may be based on the same basic formula, substituting molasses powder, oat bran and apple for the bacon. Flavorings particularly appealing to cats include artificial soy based compounds with a fish-like flavor. Human recipients may prefer sweeter flavorings, such as sugars or molasses.

The soft chews of the invention may be packaged individually for administration and stable storage. Examples of suitable packaging materials include HDPE bottles or foil/foil packaging.

B. Processes for Manufacturing Soft Chews of the Invention

Active and inactive ingredients for a soft chew of the invention are added to a mixing vessel of a horizontal mixer capable of blending the material and casting it against the side of the mixing vessels. This action permits the ingredients to be well and consistently blended without application of heat or addition of pharmaceutical grade water to the mixture.

Horizontal mixers generally comprise a mixing chamber, an elongated, horizontal mixing shaft which rotates, and a plurality of mixing tools which depend generally perpendicularly from the horizontal shaft to rotate around the inside of the chamber. (See, e.g., U.S. Pat. No. 5,735,603, the disclosure of which is incorporated herein by this reference). The mixing tools are configured and dimensioned as required for the mixing process to follow the shape of the chamber walls as rotated for proper mixing of all of material present. Some such mixing chambers are cylindrically shaped, while others are trough-shaped, such as mixers which are commonly referred to in the art as double-arm mixers or ribbon mixers.

In general, a horizontal mixer will have a horizontal mixing shaft extending out of the chamber at both ends. In a motorized mixer, at one end of the shaft, referred to as the drive end, the shaft is operably coupled to a drive motor for rotating the shaft. At the drive end, the shaft is typically coupled through a bearing structure located between the drive motor and the chamber. The bearing structure provides support of the shaft drive end and also ensures smooth rotation. A separate seal structure is often provided further in along the length of the shaft to seal it against leakage of material into and out of the mixing chamber.

A particularly preferred mixer for use in the invention used is a plough type ribbon mixer with optional agitating blades, sold under the FXM SERIES™ trademark by Littleford Day Corporation. A 200 kg capacity blender can be used for commercial scale production, and is capable of producing as little as 50 kg of chew mixture for research scale work. No heat is applied during mixing, and the blended product produced has a consistent weight, ingredient distribution and texture from batch to batch.

Preferably, dry ingredients of the chew mixture are blended first, then liquid ingredients (e.g., humectants and softening agents) are added and blended therein to form a thoroughly blended mixture. After blending, the chew mixture is discharged from a port through the blender into a suitable container for processing into individual dosage units with a forming machine.

A variety of forming equipment may be utilized in the invention, but those particularly preferred for use are molding machines developed for use in producing molded food products, such as pre-formed hamburger patties and chicken nuggets. For example, the molding machines disclosed in U.S. Pat. Nos. 3,486,186; 3,887,964; 3,952,478; 4,054,967; 4,097,961; 4,182,003; 4,334,339; 4,338,702; 4,343,068; 4,356,595; 4,372,008; 4,535,505; 4,597,135; 4,608,731; 4,622,717; 4,697,308; 4,768,941; 4,780,931; 4,818,446; 4,821,376; 4,872,241; 4,975,039; 4,996,743; 5,021,025; 5,022,888; 5,655,436; and 5,980,228 (the disclosures of which are incorporated herein) are representative of forming equipment that may be utilized in the invention.

Preferred forming equipment for use in the invention includes the Formax F6™ molding machine made by the Formax Corporation. The F6 machine has the capabilities of 60 stokes per minute. A square forming die of 6" by 6" can be used to form approximately 16 chunk-like soft chew units per stroke, each unit weighing 4 grams and being approximately ⅝" by ⅝" in size. Dies for production of other shapes (e.g., bone shaped chews) may also be utilized.

In such a machine, a rotary valve opens to cause the chew mixture to flow through fill slots beneath into a first set of mold cavities. A mold plate is advanced, forcing the chew mixture into a second set of cavities, then the mold plate is retracted so the cycle can begin again. The molding mechanism is hydraulic, and works by light pressure on the molding plate, without application of heat.

A knockout mechanism is provided with cups that align with the cavities to eject molded mixture from all the mold plate cavities simultaneously. For molding soft chews of the invention, such a machine could produce an output per hour of approximately 57,600 units, assuming use of a blender mixture yielding 50,000 units per sub batch. Each batch of chews may be packaged in bulk or, preferably, each chew is then individually packaged for storage.

The invention having been fully described, its practice is illustrated by the examples provided below. Standard abbreviations and measurements apply throughout the examples unless a contrary definition is given. The examples do not limit the scope of the invention, which is defined entirely by the appended claims.

Example 1

Ivermectin Soft Chew for Treatment of Heartworms

An example of a soft chew suitable for delivery of an active is set forth in Formula I below.

| Formula 1: | |
|---|---|
| Concentration % w/w | Ingredient |
| 47.90 | Starch 1500, USP |
| 1.0 | Powdered Sugar, USP |
| 2.0 | Oat Bran, Food Grade |
| 15.0 | Bacon Flavor (Provesta ™ 356), Food Grade |
| 2.0 | Polyethylene glycol 8000 |
| 20.0 | Glycerin, USP |
| 7.0 | Vegetable Oil (soybean), USP |
| 0.1 | Tenox 4, Food Grade |
| 1.0 | Magnesium Stearate, USP |
| 1.0 | Yeast Flavoring |
| 3.0 | Croscarmellose, sodium N.F. |
| 0.001 | FD&C Carmine Dye |

Example 2

Method for Coating Active Ingredients of Soft Chews of the Invention

The active (ivermectin) was milled and screened through a 20 mesh screen. A 10% trituration was made by dry blending 100 grams of ivermectin and 900 grams of Starch 1500 for 3 to 5 minutes. The resultant trituration was fluidized in a fluidized bed column and a food grade coating (OPADRY™) was applied using a Wurster coater, a top spray fluidized coater, or other suitable device.

Example 3

Exemplary Method of Manufacture for Soft Chews of the Invention

All dry ingredients listed in Examples 1 and 2 except the oat bran were sifted through a 20 mesh screen, then placed with the bran into the mixing vessel of a horizontal mixing blender and mixed for 5 minutes. The glycerin was added slowly followed by the slow addition of the vegetable oil and Tenox 4 which had been added to the oil. The product was mixed for 3 minutes. The PEG 8000 was melted then added relatively quickly to the chew mixture, which was then mixed for an additional minute. The mixture resembled a "cookie dough-like" appearance.

The mixture was formed into individual chunks using a Formax F6™ molding machine with dies for production of chunk-like shapes, and packaged for storage.

The invention having been fully described, its scope is defined by the claims appended hereto.

The invention that is claimed is:

1. A process for manufacturing multiple units of an edible soft chewable medication ("soft chewable") having consistent composition and weight, the method comprising:
    (a) providing ingredients for the soft chewable to the mixing chamber of a mixer, wherein the ingredients consist of (i) 0.001 to 75% of an anti-parasiticidal or antibiotic active agent, wherein the active agent is adversely affected by temperatures typically generated by extrusion, is not palatable, or both; and (ii) palatable food grade dry inactive ingredients including at least one each of a flavoring, a binder, a bulking agent, a humectant, an oil and an excipient;
    (b) blending the active agent and dry inactive ingredients in the mixing chamber by casting the ingredients against the walls of the mixing chamber space, wherein operation of the low shear mixer causes an edible dry soft chew mixture to be formed having the active ingredient uniformly blended therein;
    (c) adding a first softening agent consisting of polyethylene glycol or paraffin wax, together with 1 to 3% w/w of a further softening agent selected from the group consisting of propylene glycol, magnesium stearate, calcium stearate or sodium lauryl sulfate to the dry mixture and blending the ingredients together within the mixer to form a soft chewable mixture having a meat-like texture;
    (d) removing the soft chewable mixture from the mixer; and,
    (e) molding the edible soft chewable mixture into individual unit masses without need for prior cooling of the chewable mixture or application of compression heat thereto, wherein the unit masses so formed are of consistent weight and active content from unit to unit and are generally more palatable to cats and dogs than tablet dosage forms of the active agent,
    wherein no cooking extrusion is performed during practice of the method, and wherein further no water or animal origin ingredients are added to the active agent or mixture during performance of the method.

2. The process according to claim 1, further comprising the step of preparing a trituration of the active agent with an excipient before the active agent is added to the mixing chamber in step (a).

3. The process according to claim 1, wherein the softening agent added in step (c) is polyethylene glycol.

4. The process according to claim 1 or claim 2, further comprising the step (a)' of coating the active agent with a food grade coating before the active agent is added to the mixing vessel in step (a).

5. The process according to claim 1, further comprising step (f) wherein the individual unit masses are placed into a pharmaceutically acceptable container.

6. The process according to claim 1, wherein the inactive ingredients are irradiated or pasteurized.

7. The process according to claim 1, wherein the flavoring is a soy protein product.

8. The process according to claim 7, wherein the flavoring is an artificially bacon flavored soy protein powder.

9. The process according to claim 1, wherein the humectant is glycerol, glycerin or cetyl alcohol.

10. The process according to claim 1, wherein the pharmaceutically active agent is prepared in a trituration with an excipient.

11. The process according to claim 1, wherein the pharmaceutically active agent is coated.

12. The process according to claim 1, further comprising a preservative.

13. The process according to claim 1, wherein the excipient is at least one of crosprovidone, croscarmellose sodium, cellulose, starch, partially or fully pregelatinized starch, and sodium starch glycolate.

14. The process according to claim 1, wherein the softening agent comprises polyethylene glycol.

15. The process according to claim 1, wherein the softening agent further comprises magnesium stearate.

16. The process according to claim 9, wherein the humectant is glycerin.

17. The process according to claim 13, wherein the excipient comprises pregelatinized starch.

18. The process according to claim 17, wherein the excipient further comprises croscarmellose sodium.

19. The process according to claim 1, wherein the oil is a vegetable oil.

20. The process according to claim 1, wherein the bulking agent is bran, meal, flour, cereal, fiber, whole grains, vegetables, seeds, gum arabic, pectins, modified starches, alginates, carrageenans, xanthan gums, carboxymethylcellulose, methylcellulose, hycroxyethylcellulose, hydroxypropylcellulose, propylene glycol alginate, polyvinylpyrrolidone, carboxyvinyl polymers, polyethylene oxide polymers, talc, dicalcium phosphate and antacids.

21. The process according to claim 12, wherein the preservative is potaasium sorbate, sodium benzoate or calcium propionate.

22. The process according to claim 12, wherein the preservative is a food combination of BHA and BHT anti-oxidants.

23. The process according to claim 1, wherein the flavoring is at least one of plant proteins, plant oils, carob, peanuts, fruit flavors, sweeteners, herbs and spices.

24. The process according to claim 1, wherein the binder is at least one of molasses, corn syrup, peanut butter, food gum, starch, honey, maple syrup, sugar and pregelatinzed corn starch.

25. The process according to claim 1, wherein the active agent is an anti-parasticidal.

26. The process according to claim 25, wherein the anti-parasitcidal agent is ivermectin.

* * * * *